United States Patent
Marczyk et al.

(10) Patent No.: US 10,271,836 B2
(45) Date of Patent: Apr. 30, 2019

(54) POWERED ENDOSCOPIC SUTURING DEVICE

(71) Applicant: Covidien LP, Mansfield, MA (US)

(72) Inventors: Stanislaw Marczyk, Stratford, CT (US); Russell Pribanic, Roxbury, CT (US); Anthony Calderoni, Bristol, CT (US); Christopher Switalski, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 250 days.

(21) Appl. No.: 15/353,893

(22) Filed: Nov. 17, 2016

(65) Prior Publication Data

US 2017/0150961 A1    Jun. 1, 2017

Related U.S. Application Data

(60) Provisional application No. 62/261,428, filed on Dec. 1, 2015.

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0625* (2013.01); *A61B 17/06066* (2013.01);
(Continued)

(58) Field of Classification Search
CPC .......... A61B 17/0469; A61B 17/06066; A61B 17/0625; A61B 2017/0609;
(Continued)

(56) References Cited

U.S. PATENT DOCUMENTS 5,478,344 A    12/1995    Stone et al.
5,735,862 A    4/1998    Jennings et al.
(Continued)

FOREIGN PATENT DOCUMENTS

DE    4139628 C1    3/1993
WO    2011/024036 A1    3/2011

OTHER PUBLICATIONS

European Search Report issued in corresponding European Appln. No. 16201455.9 dated Feb. 22, 2017.

*Primary Examiner* — Julian W Woo

(57) ABSTRACT

An endoscopic stitching device includes an actuation shaft, a tool assembly, and a drive assembly. The tool assembly includes a suture needle and a pair of jaws transitionable between open and closed positions. Each jaw includes a needle engaging blade slidably supported thereon. Each needle engaging blade is transitionable between an extended position in which the needle engaging blade engages the suture needle and a retracted position in which the needle engaging blade is disengaged from the suture needle. The drive assembly includes first, second, and third electrical actuators. The first actuator is operatively coupled with the actuation shaft to cause axial displacement of the actuation shaft. The axial displacement of the actuation shaft causes opening and closing of the pair of jaws. The second and third actuators are operatively coupled with the needle engaging blades to provide axial displacement of the needle engaging blades.

15 Claims, 7 Drawing Sheets

(51) Int. Cl.
*A61B 17/06* (2006.01)
*A61B 17/00* (2006.01)

(52) U.S. Cl.
CPC ............... *A61B 2017/00367* (2013.01); *A61B 2017/00371* (2013.01); *A61B 2017/00398* (2013.01); *A61B 2017/00734* (2013.01); *A61B 2017/047* (2013.01); *A61B 2017/0609* (2013.01)

(58) Field of Classification Search
CPC ........... A61B 2017/00398; A61B 2017/00367; A61B 2017/00734; A61B 2017/00371; A61B 2017/047
See application file for complete search history.

(56) References Cited

U.S. PATENT DOCUMENTS

| | | | |
|---|---|---|---|
| 5,984,932 A | 11/1999 | Yoon | |
| 6,206,894 B1 | 3/2001 | Thompson et al. | |
| 6,270,508 B1 | 8/2001 | Klieman et al. | |
| 6,325,808 B1* | 12/2001 | Bernard | A61B 17/0469 318/568.11 |
| 8,177,794 B2 | 5/2012 | Cabrera et al. | |
| 8,226,667 B2 | 7/2012 | Viola et al. | |
| 8,246,637 B2 | 8/2012 | Viola et al. | |
| 8,292,905 B2 | 10/2012 | Taylor et al. | |
| 8,292,906 B2 | 10/2012 | Taylor et al. | |
| 8,337,515 B2 | 12/2012 | Viola et al. | |
| 8,372,090 B2 | 2/2013 | Wingardner et al. | |
| 8,454,631 B2 | 6/2013 | Viola et al. | |
| 8,460,275 B2 | 6/2013 | Taylor et al. | |
| 8,490,713 B2 | 7/2013 | Furnish et al. | |
| 8,496,674 B2 | 7/2013 | Cabrera et al. | |
| 8,506,581 B2 | 8/2013 | Wingardner, III et al. | |
| 8,628,545 B2 | 1/2014 | Cabrera et al. | |
| 8,636,752 B2 | 1/2014 | Cabrera et al. | |
| 8,702,732 B2 | 4/2014 | Woodard, Jr. et al. | |
| 8,747,424 B2 | 6/2014 | Taylor et al. | |
| D708,746 S | 7/2014 | Cabrera et al. | |
| 8,864,776 B2 | 10/2014 | Bogart et al. | |
| 8,968,340 B2 | 3/2015 | Chowaniec et al. | |
| 8,968,342 B2 | 3/2015 | Wingardner, III et al. | |
| 9,113,860 B2 | 8/2015 | Viola et al. | |
| 9,271,723 B2 | 3/2016 | Taylor et al. | |
| 9,585,659 B2* | 3/2017 | Viola | A61B 17/07207 |
| 10,064,640 B2* | 9/2018 | Tuijthof | A61B 17/29 |
| 2010/0010512 A1* | 1/2010 | Taylor | A61B 17/04 606/144 |
| 2010/0228270 A1 | 9/2010 | Bogart et al. | |
| 2011/0040308 A1 | 2/2011 | Cabrera et al. | |
| 2012/0215234 A1 | 8/2012 | Chowaniec et al. | |
| 2013/0245643 A1 | 9/2013 | Woodard, Jr. et al. | |
| 2013/0282027 A1 | 10/2013 | Woodard, Jr. et al. | |
| 2013/0282031 A1 | 10/2013 | Woodard, Jr. et al. | |
| 2013/0310848 A1 | 11/2013 | Furnish et al. | |
| 2015/0142018 A1 | 5/2015 | Sniffin et al. | |
| 2018/0249999 A1* | 9/2018 | Parihar | A61B 17/1155 |

\* cited by examiner

POWERED ENDOSCOPIC SUTURING DEVICE

CROSS-REFERENCE TO RELATED APPLICATIONS

This application claims the benefit of and priority to U.S. Provisional Patent Application No. 62/261,428, filed Dec. 1, 2015, the entire disclosure of which is incorporated by reference herein.

BACKGROUND

Technical Field

The present disclosure relates to surgical instruments and, more particularly, to endoscopic suturing and/or stitching devices.

Background of Related Art

In many surgical procedures, it is often necessary to suture bodily organs or tissue. It is especially challenging during endoscopic surgery because of the small openings through which the suturing of bodily organs or tissues must be accomplished. Hand-held and hand-actuated or hand-powered endoscopic stitching devices have been developed to facilitate the suturing process. For a detailed discussion of exemplary hand-held and hand-actuated or hand-powered endoscopic stitching devices, reference may be made to U.S. Pat. No. 5,478,344, filed on Aug. 19, 1994, and U.S. Pat. No. 8,628,545, filed on Jun. 10, 2009, the entire content of each of which is incorporated herein by reference.

However, a need still exists for improvements in suturing devices to further facilitate and expedite the suturing process.

SUMMARY

The present disclosure describes a powered suturing device that demonstrates a practical approach to meeting the performance requirements and overcoming the usability challenges associated with suturing devices. In general, the present disclosure describes powered suturing devices that include a handle assembly including a drive mechanism, an elongate member, and an end effector having a pair of jaws to engage a suture needle.

In accordance with an embodiment of the present disclosure, there is provided an endoscopic stitching device including an actuation shaft, a tool assembly, and a drive assembly. The tool assembly includes a suture needle and a pair of jaws transitionable between open and closed positions. Each jaw of the pair of jaws includes a needle engaging blade slidably supported thereon. Each needle engaging blade is transitionable between an extended position in which the needle engaging blade engages the suture needle and a retracted position in which the needle engaging blade is disengaged from the suture needle. The drive assembly includes first, second, and third electrical actuators. The first actuator is operatively coupled with the actuation shaft to cause axial displacement of the actuation shaft. The axial displacement of the actuation shaft causes opening and closing of the pair of jaws. The second and third actuators are operatively coupled with the needle engaging blades to provide axial displacement of the needle engaging blades.

The drive assembly may further include a printed circuit board including a microprocessor to control execution of at least one of the first, second, or third actuators. The drive assembly may also include a control interface including first and second buttons. Actuation of the first button may cause reciprocating axial displacement of the needle engaging blades. Actuation of the second button may transition the pair of jaws between the open and closed positions. Alternatively, actuation of the first button may transition the pair of jaws between open and closed positions and cause reciprocating axial displacement of the needle engaging blades.

In an embodiment, the drive assembly may further include a battery pack to supply power to the first, second, and third actuators.

In an embodiment, each jaw of the pair of jaws may define a needle receiving recess dimensioned to receive a portion of the suture needle.

In an embodiment, at least one of the first, second, or third actuators may be a servomotor.

In an embodiment, the drive assembly may further include a first lead screw and a first nut. In particular, the first actuator may be operatively connected to the first lead screw. The first nut may be operatively connected to the actuation shaft. Actuation of the first actuator may cause rotation of the first lead screw, which, in turn may cause the axial displacement of the actuation shaft.

In an embodiment, the drive assembly may further include a second lead screw and a second nut, with the second actuator being operatively connected to the second lead screw. The second nut may be operatively connected to one of the needle engaging blades. Actuation of the second actuator may cause rotation of the second lead screw, which, in turn may cause axial displacement of one of the needle engaging blades.

In an embodiment, the drive assembly may further include a third lead screw and a third nut. In particular, the third actuator may be operatively connected to the third lead screw. The third nut may be operatively connected to the other one of the needle engaging blades. Actuation of the third actuator may cause rotation of the third lead screw, which, in turn may cause axial displacement of the other one of the needle engaging blades.

In accordance with another embodiment of the present disclosure, there is provided an endoscopic stitching device including a handle assembly, an elongate member, and a tool assembly. The handle assembly includes a drive assembly including first, second, and third electrical actuators. The elongate member has an actuation shaft. The elongate member extends from the handle assembly. The tool assembly is operatively supported on the elongate member. The tool assembly includes a suture needle and a pair of jaws pivotally associated with one another. Each jaw of the pair of jaws includes a needle engaging blade slidably supported thereon. Each needle engaging blade is transitionable between an extended position in which the needle engaging blade engages the suture needle and a retracted position in which the needle engaging blade is disengaged from the suture needle. The first actuator is operatively coupled with the actuation shaft, such that axial displacement of the actuation shaft results in opening and closing of the pair of jaws. The second and third actuators are operatively coupled with the respective needle engaging blades to provide axial displacement of the needle engaging blades.

BRIEF DESCRIPTION OF THE DRAWINGS

The accompanying drawings, which are incorporated in and constitute a part of this specification, illustrate embodiments of the disclosure and, together with a general description of the disclosure given above, and the detailed descrip

DETAILED DESCRIPTION

Figure 1:
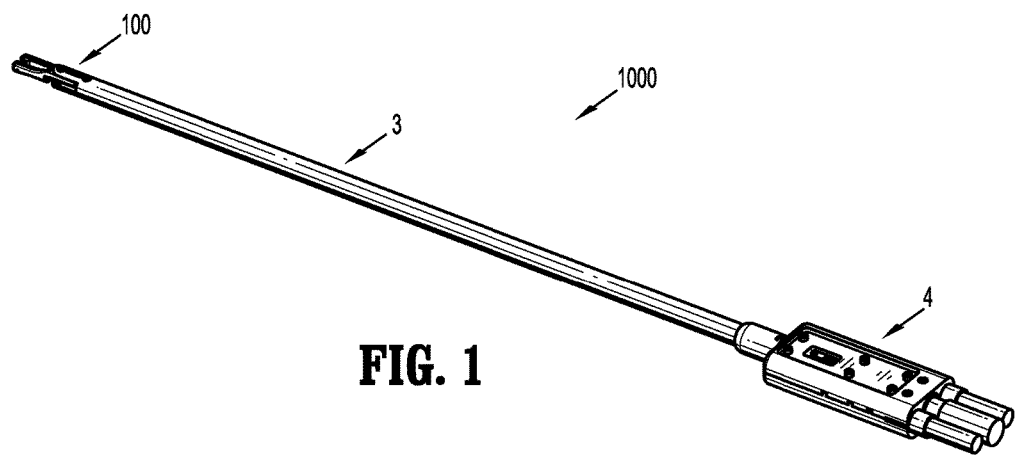
- FIG. 1 is a powered endoscopic suturing device in accordance with an embodiment of the present disclosure illustrating the powered endoscopic suturing device with a handle assembly housing removed.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

Figure 2:
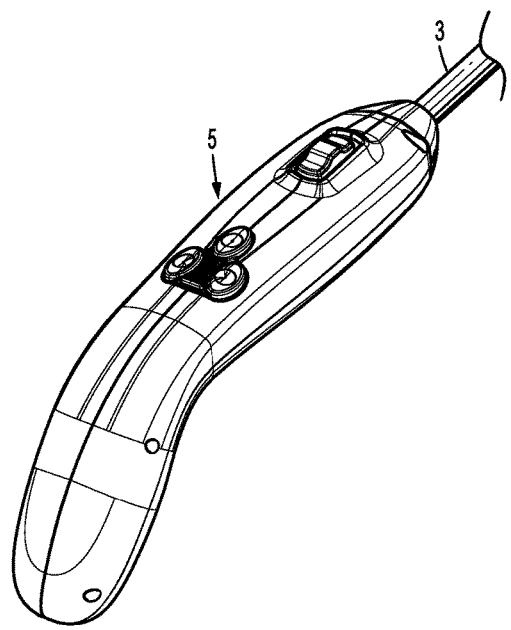
FIG. 2 is a perspective view of a handle assembly for use with the powered endoscopic suturing device of FIG. 1.
Figure 3:
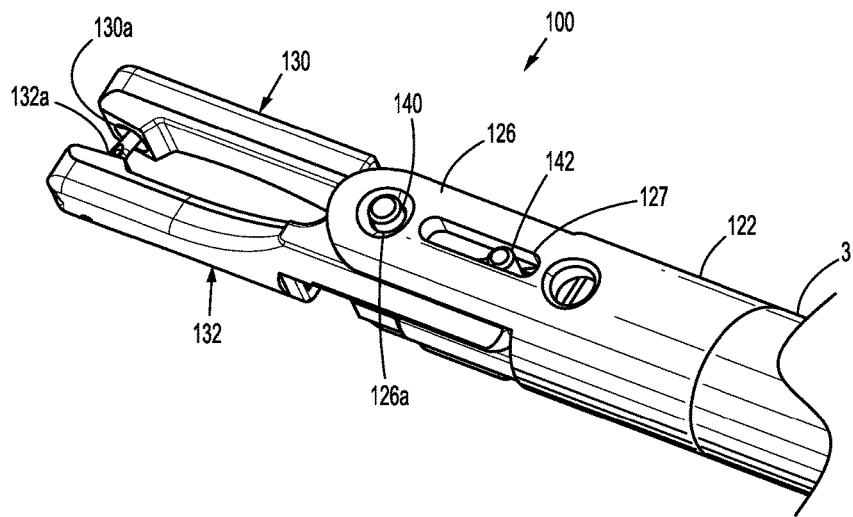
FIG. 3 is a partial, perspective view of an elongate member and an end effector of the powered endoscopic suturing device of FIG. 1.

With reference to FIGS. 1-3, there is illustrated a powered suturing device 1000 in accordance with an embodiment of the present disclosure. Powered suturing device 1000 includes a handle assembly 5 (FIG. 2) including a motor housing 4 (FIG. 1) therein. An elongate shaft 3 extends from handle assembly 5 and supports an end effector 100 at a distal end thereof.

Figure 4:
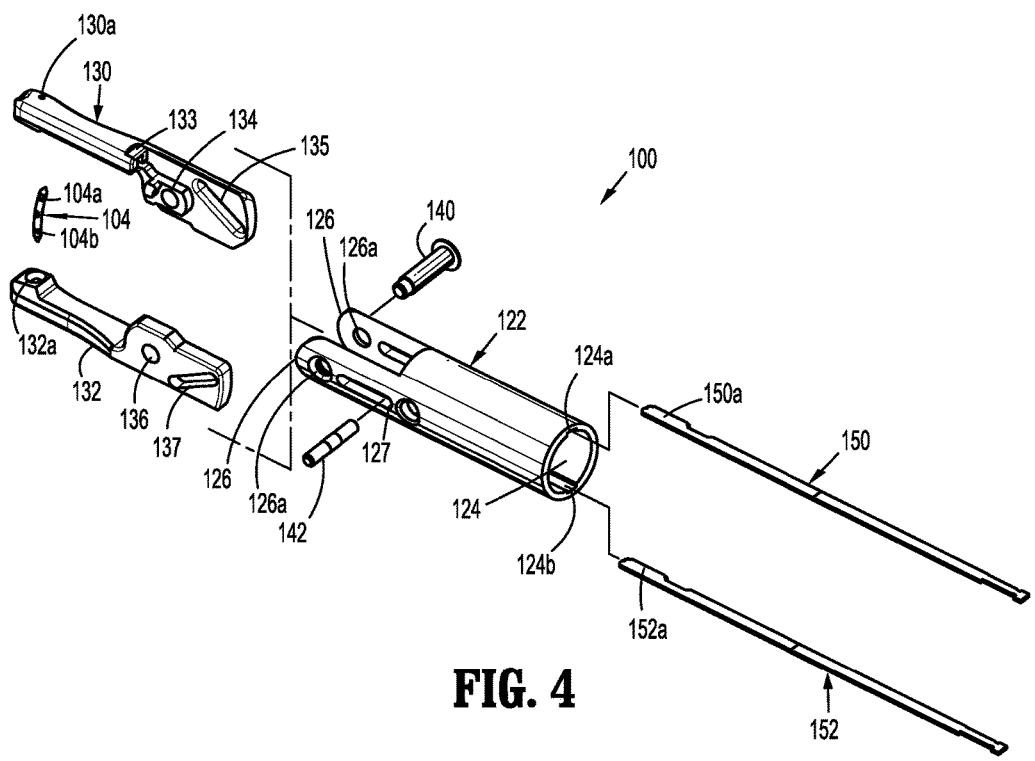
FIG. 4 is an exploded perspective view of the end effector of FIG. 1 with parts separated.

With reference now to FIGS. 3 and 4, end effector 100 includes a jaw support member 122 and first and second jaws 130, 132 pivotably mounted on jaw support member 122. Jaw support member 122 defines a lumen 124 (FIG. 4) in communication with a channel (not shown) defined in elongate shaft 3 (FIG. 3). Jaw support member 122 further includes a pair of spaced apart arms 126. Each arm 126 defines a hole 126a and a camming slot 127 extending along a length of jaw support member 122. Jaw support member 122 further defines a pair of opposing grooves 124a, 124b configured to slidably receive respective first and second needle engaging blades 150, 152.

With particular reference to FIG. 4, first and second jaws 130, 132 include respective first and second needle receiving recesses 130a, 132b configured to receive at least a portion of a surgical needle 104. First and second jaws 130, 132 further define respective pivot holes 134, 136 and respective camming slots 135, 137. Camming slots 135, 137 define an acute angle with respect to each other. First and second jaws 130, 132 are supported on jaw support member 122 by a pivot pin 140 that extends through holes 126a defined in respective arms 126 of support member 122 and pivot holes 134, 136 defined in respective first and second jaws 130, 132. Camming pin 142 is slidably disposed in camming slots 135, 137 of respective first and second jaws 130, 132 and camming slots 127 of jaw support member 122. Under such a configuration, axial displacement of camming pin 142 transitions first and second jaws 130, 132 between an open position and a closed position. Camming pin 142 is coupled with a center rod 52 (FIG. 9) that extends from motor housing 4 and through elongate shaft 3. Axial displacement of center rod 52 provides concomitant axial displacement to camming pin 142 to transition first and second jaws 130, 132 between the open and closed positions. For example, jaws 130, 132 may be maintained in the open position by having center rod 52 at a distal-most position which, in turn, positions camming pin 142 at a distal-most end of camming slots 135, 137 of first and second jaws 130, 132 and camming slot 127 of jaw support member 122.

With continued reference to FIG. 4, end effector 100 further includes first and second needle engaging blades 150, 152. First and second needle engaging blades 150, 152 are individually transitionable between an extended position and a retracted position. First and second needle engaging blades 150, 152 are slidably supported within respective grooves 124a, 124b of support member 122 for concomitant or reciprocating movement. For example, needle engaging blades 150, 152 may move in opposite directions to perform suturing or move in the same direction to, e.g., secure suture needle 104 with first and second jaws 130, 132 to enable the clinician to tighten suture 105 (FIG. 5) or to disengage suture needle 104 from first and second jaws 130, 132 to enable the clinician to replace suture needle 104. First and second needle engaging blades 150, 152 are configured to further extend into blade receiving channels 133 (only shown in first jaw 130) of respective first and second jaws 130, 132. Blade receiving channels 133 are dimensioned and configured to at least partially intersect the respective first and second needle recesses 130a, 132a. Under such a configuration, by advancing first and second needle engaging blades 150, 152 within respective channels 133, distal ends 150a, 152a of respective first and second needle engaging blades 150, 152 engage respective notches 104a, 104b defined in suture needle 104 when at least a portion of suture needle 104 is disposed within the respective recesses 130a, 132a of first and second jaws 130, 132. Reciprocating movement of first and second needle engaging blades 150, 152 causes, for example, engagement of first needle engaging blades 150 with suture needle 104 and disengagement of second needle engaging blade 152 from suture needle 104, or vice versa.

Figure 5:
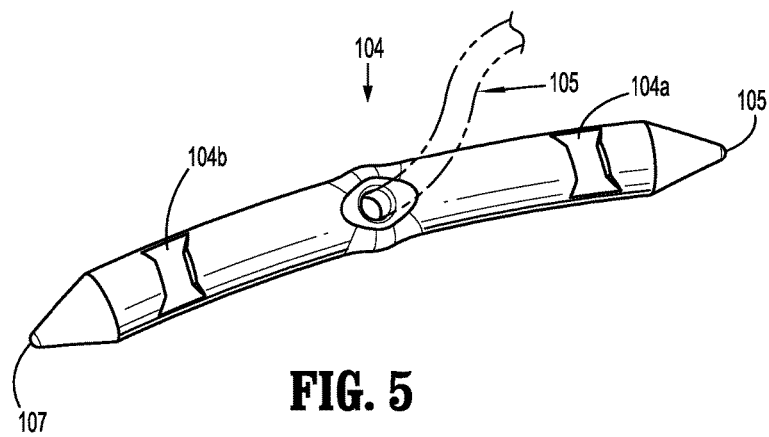
FIG. 5 is a perspective view of a suture needle of the end effector of FIG. 3.

With reference now to FIG. 5, suture needle 104 defines notches 104a, 104b at respective opposite ends 105, 107 of suture needle 104. A suture 105 (shown in phantom) is secured to surgical needle 104 at a location between notches 104a, 104b. Suture 105 may include barbs (not shown) to inhibit movement of suture 104 in a particular direction. Reference may be made to U.S. Pat. No. 8,628,545, filed on Jun. 10, 2009, entitled "ENDOSCOPIC STITCHING DEVICES," the entire content of which is incorporated herein by reference, for a detailed discussion of the construction and operation of end effector 100.

Figure 8:
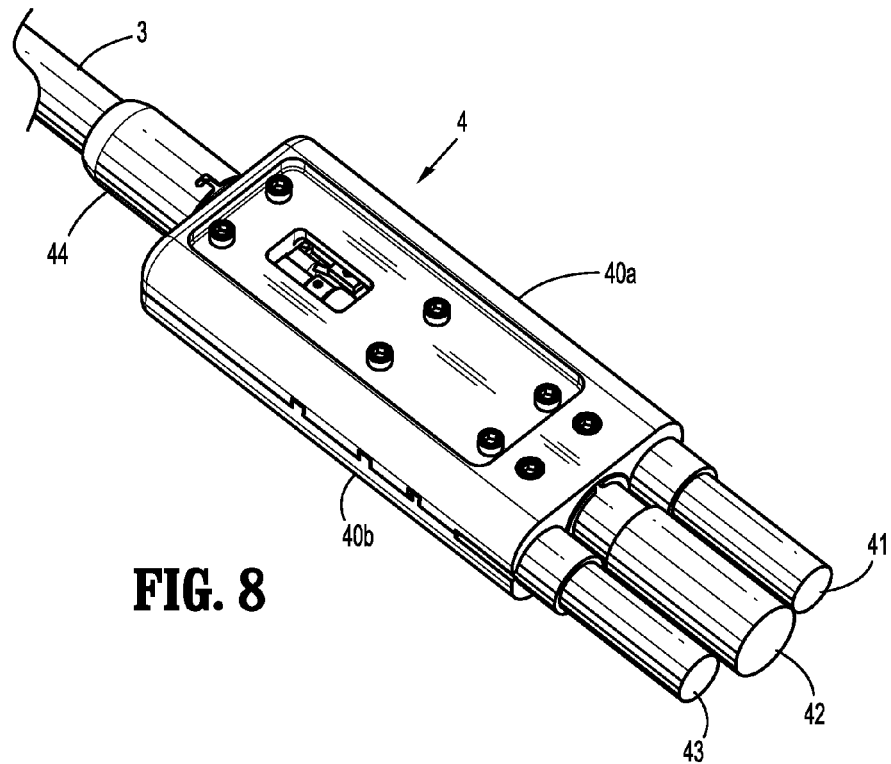
FIG. 8 is a perspective view of a motor housing of the powered endoscopic suturing device of FIG. 1.
Figure 9:
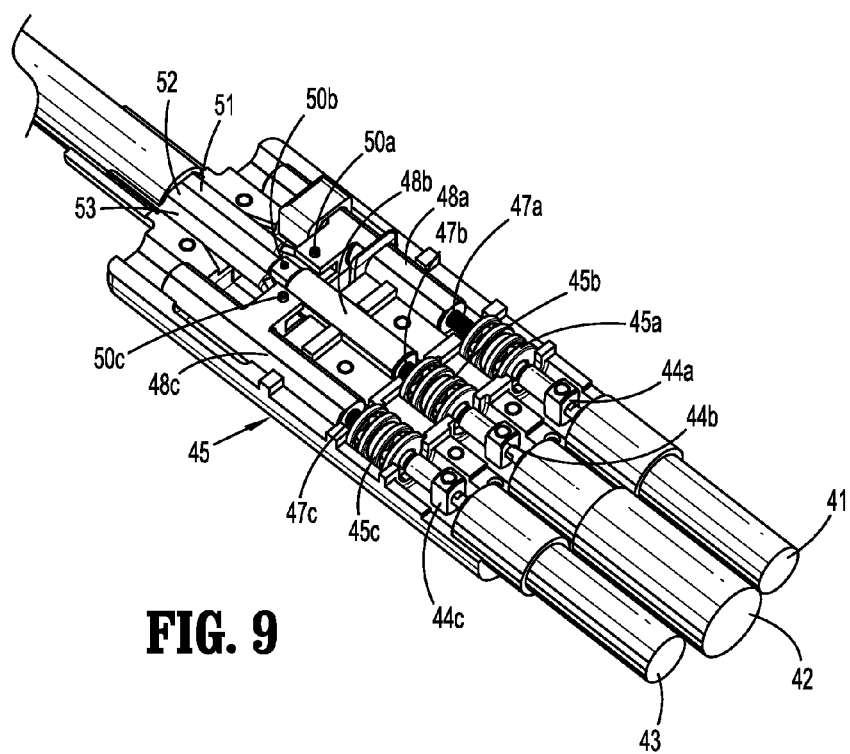
FIG. 9 is a perspective view of the motor housing of FIG. 8 with a cover removed illustrating a drive assembly of the powered endoscopic suturing device of FIG. 1.

With reference now to FIGS. 8 and 9, motor housing 4 includes two body halves 40a, 40b coupled by a locking sleeve 44. Motor housing 4 includes a drive mechanism 45 (FIG. 9) to open or close first and second jaws 130, 132 and actuate first and second needle engaging blades 150, 152. Drive mechanism 45 includes a plurality of motors 41, 42, 43. Each motor 41, 42, 43 may be a servomotor, such as, e.g., a DC brushless motor with or without Hall Effect sensors.

Figure 6:
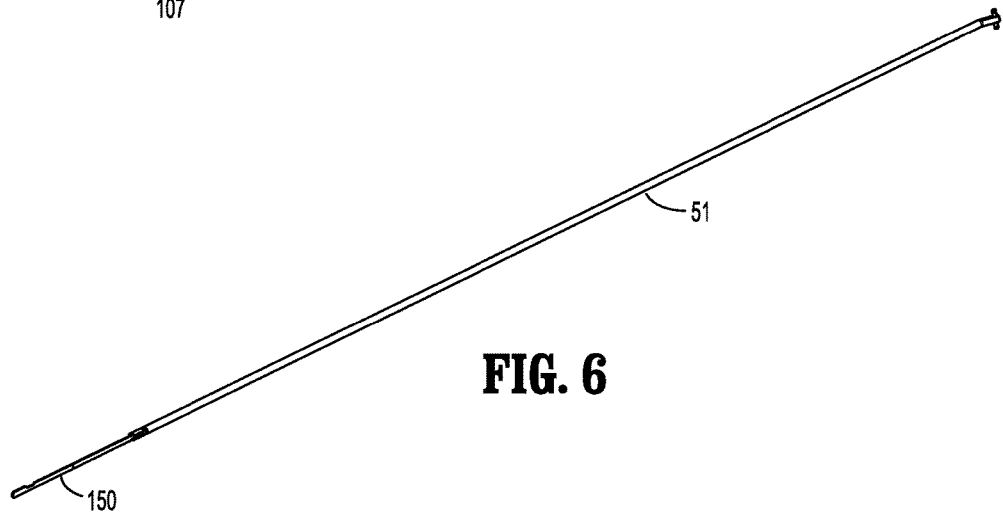
FIG. 6 is a perspective view of a needle engaging blade and a rod coupled to the needle engaging blade of the powered endoscopic suturing device of FIG. 1.
Figure 7:
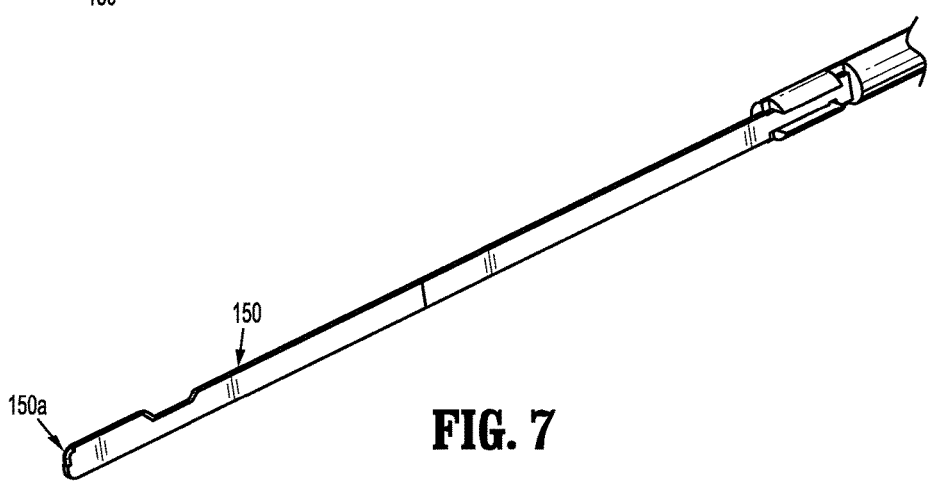
FIG. 7 is a partially enlarged perspective view of the needle engaging blade of FIG. 6.

Each motor 41, 42, 43 is operatively coupled with a respective connecting sleeve 44a, 44b, 44c, a respective lead screw 47a, 47b, 47c, and a respective set of thrust bearings with disc springs 45a, 45b, 45c. Each lead screw 47a, 47b, 47c is operatively coupled with a respective nut 48a, 48b, 48c. Under such a configuration, rotational output of each motor 41, 42, 43 provides concomitant rotation to the respective lead screw 47a, 47b, 47c, which, in turn, causes axial displacement of the respective nut 48a, 48b, 48c. In particular, nut 48b is coupled with center rod 52 by a pin 50b. Center rod 52 is coupled with camming pin 142 (FIG. 3), such that axial displacement of center rod 52 transitions first and second jaws 130, 132 between the open and closed positions. Nuts 48a, 48c are coupled with rods 51, 53, by pins 50a, 50c, respectively. Rods 51, 53 are coupled with the respective first and second needle engaging blades 150, 152 such that axial displacement of rods 51, 53 causes concomitant axial displacement of the respective first and second needle engaging blades 150, 152. Rods 51, 53 are substantially similar and, thus, only rod 51 and first needle engaging blade 150 are shown in FIGS. 6 and 7.

Figure 10:
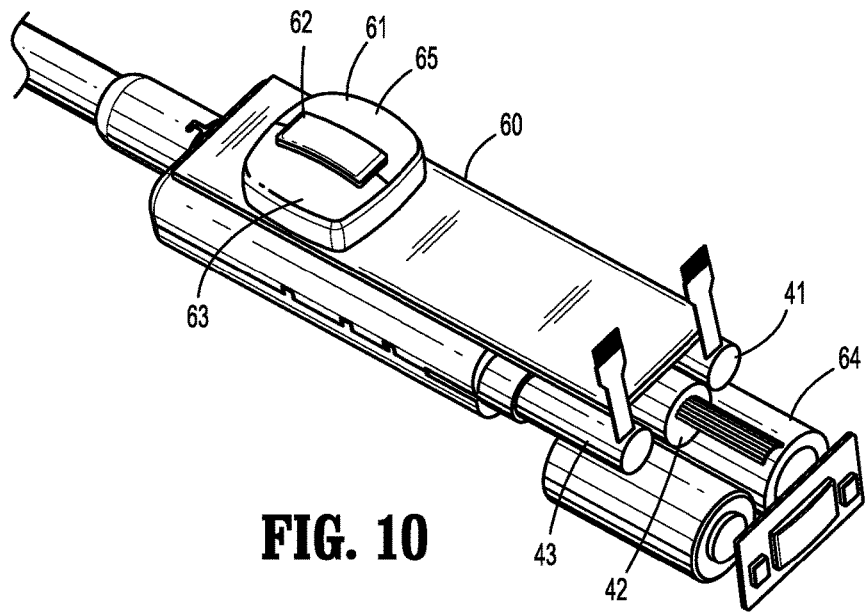
FIG. 10 is a perspective view of the motor housing of FIG. 8 including an actuation interface and a battery pack.

With reference now to FIG. 10, handle assembly 5 (FIG. 2) further includes a printed circuit board 60 including a microprocessor. The microprocessor controls drive mechanism 45 (FIG. 9). In particular, the microprocessor controls the execution and sequence of execution of suturing such as, e.g., concomitant or reciprocating movements of first and second needle engaging blades 150, 152.

Figure 11:
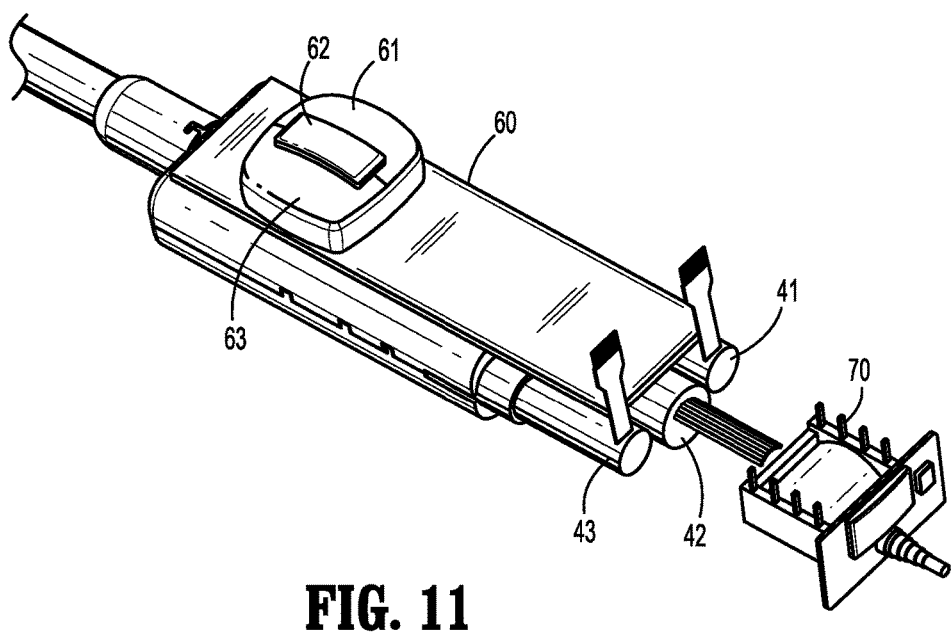
FIG. 11 is a perspective view of the motor housing of FIG. 8 including a transformer.

With continued reference to FIG. 10, printed circuit board 60 may further include control panel 65 including control buttons 61, 62, 63. Each control button 61, 62, 63 may be utilized to actuate one or more motors 41, 42, 43. For example, control button 62 may be used to actuate motor 42 to open and close first and second jaws 130, 132. Control buttons 61, 63 may be used to cause reciprocating axial displacement of first and second needle engaging blades 150, 152 toward and away from the respective aperture 130a, 132a (FIGS. 3 and 4) of first and second jaws 130, 132 to engage or disengage from the respective notches 104a, 104b of suture needle 104. Drive mechanism 45 and the microprocessor may be powered by a battery pack 64. Alternatively, a transformer 70 (FIG. 11) may be utilized to draw power from an external power supply.

In use, control button 62 is pressed to open first and second jaws 130, 132. Initially, suture needle 104 must be lodged into one of first or second jaws 130, 132. For the illustration purposes, suture needle 104 is lodged into first jaw 130. At this time, first needle engaging blade 150 moves to the extended position and engages notch 104a of suture needle 104 to secure suture needle 104 with first jaw 130, and second needle engaging blade 152 moves to the retracted position to be disengaged from notch 104b of suture needle 104. Then, control button 62 may be pressed to close first and second jaws 130, 132, during which suture needle 104 may be passed through tissue and end 107 (FIG. 5) of suture needle 104 is received in aperture 132a of second jaw 132. At this time, control button 63 is pressed to transition second needle engaging blade 152 to the extended position to engage notch 104b of suture needle 104 and to transition first needle engaging blade 150 to the retracted position to disengage from notch 104a of suture needle 104. In this manner, suture needle 104 is secured with second jaw 132. Thereafter, control button 62 is pressed again to open first and second jaws 130, 132. The clinician may repeat this process to perform as much suturing as needed.

Figure 12:
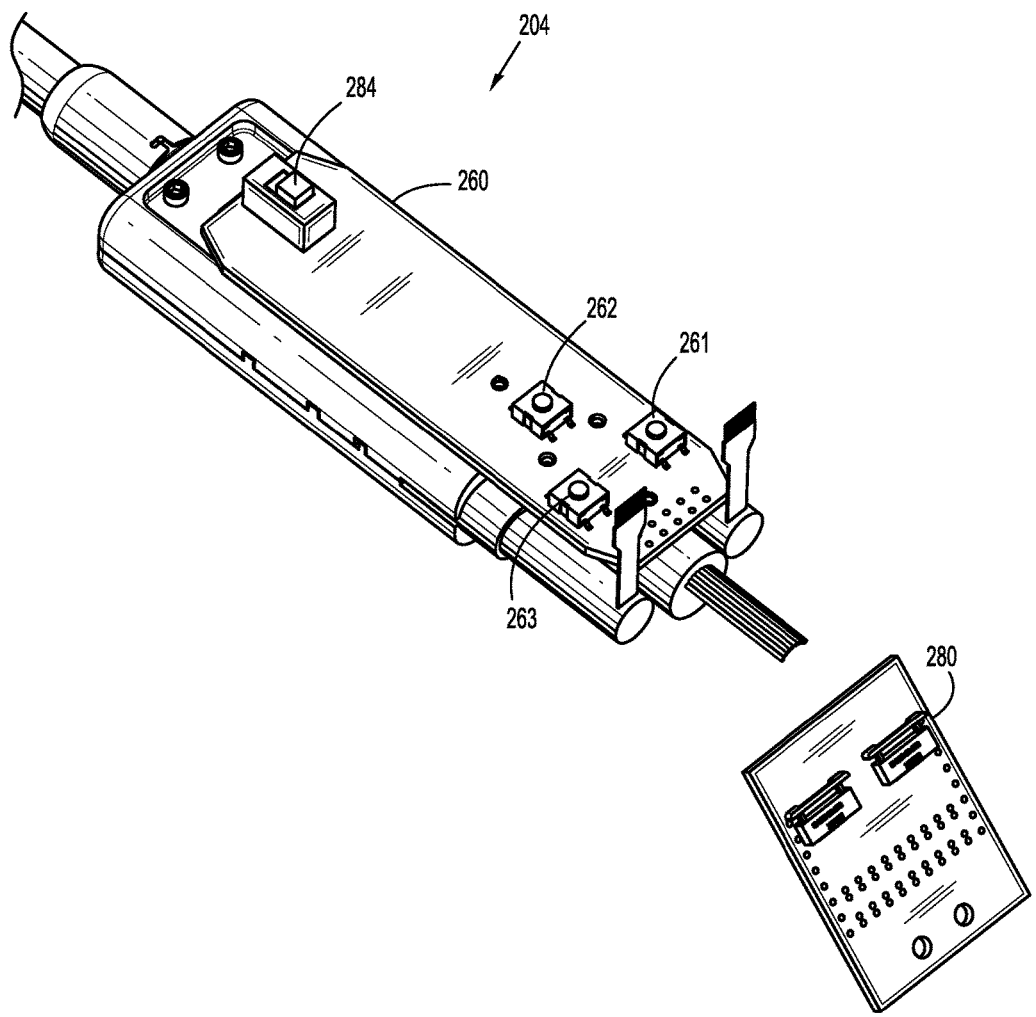
FIG. 12 is a perspective view of another motor housing of FIG. 8 including an actuation interface in accordance with another embodiment of the present disclosure.

With reference now to FIG. 12, there is provided a motor housing 204 in accordance with another embodiment of the present disclosure. Motor housing 204 includes first and second printed circuit boards 260, 280. First printed circuit board 260 includes, e.g., tactile, switches 261, 262, 263 similar to control buttons 61, 62, 63 described hereinabove, and a sliding switch 284 configured to switch between a suturing mode and a needle reloading mode. Second printed circuit board 280 may be used to house motor contacts and provide connection to an external power supply.

In order to perform suturing, sliding switch 284 is switched to the suturing mode. Switch 261 may be pressed to transition first and second jaws 130, 132 to the open position. At this time, suture needle 104 is secured with first jaw 130 in the manner described above. When switch 263 is pressed, first and second jaws 130, 132 close onto tissue, and end 107 (FIG. 5) of suture needle 104 is passed through the tissue and received in needle receiving recess 132a of second jaw 132. At this time, first needle engaging blade 150 moves to the retracted position and disengages from notch 104a of suture needle 104, and second needle engaging blade 152 moves to the extended position and engages notch 104b of suture needle 104 such that suture needle 104 is secured with second jaw 132. Upon securement of suture needle 104 on second jaw 132, first and second jaws 130, 132 transition back to the open position, and suture needle 104 is pulled through the tissue. The clinician may repeat this process as needed to complete the suturing process.

When switch 262 is pressed, first and second jaws 130, 132 close and both first and second needle engaging blades 150, 152 engage the respective notches 104a, 104b of suture needle 104. When suture needle 104 is secured to both first and second jaws 130, 132, the clinician may tighten the stitches of suture 105 and/or a knot formed by suture 105.

In order to replace suture needle 104, sliding switch 284 is switched to the reloading mode. In this mode, first and second jaws 130, 132 close, and first and second needle engaging blades 150, 152 transition to the retracted position and disengage from the respective notches 104a, 104b of suture needle 104. The clinician may press switches 261, 263 to open first and second jaws 130, 132. At this time, first and second needle engaging blades 150, 152 remain disengaged from the respective notches 104a, 104b of suture needle 104. The clinician may replace suture needle 104. After replacing the needle, switch 262 may be pressed to close first and second jaws 130, 132. Thereafter, the clinician may slide switch 284 to the suturing mode causing first and second needle engaging blades 150, 152 to engage the respective notches 104a, 104b of suture needle 104, while first and second jaws 130, 132 remain closed.

In use, switch 284 is switched to the suturing mode. At this time, suture needle 104 is secured only with first jaw 130, and first and second jaws 130, 132 open. The clinician may position suture needle 104 adjacent tissue (e.g., tissue is disposed between jaws 130, 132) such that when switch 263 is pressed, suture needle 104 passes through tissue and first and second jaws 130, 132 close onto the tissue. At this time, first needle engaging blade 150 disengages from notch 104a of suture needle 104, and second needle engaging blade 152 engages notch 104b of suture needle 104 such that suture needle 104 is secured with second jaw 132. Thereafter, first and second jaws 130, 132 reopen and suture needle 104 is pulled through the tissue by second jaw 132. The clinician may repeat this process as much as needed to achieve the desired suturing. The clinician can tighten the stitches of suture 105 or a knot of suture 105 by first pressing switch 262. When switch 262 is pressed, first and second jaws 130, 132 close and both first and second needle engaging blades 150, 152 move to the extended position and engage the respective notches 104a, 104b of suture needle 104. In addition, the clinician may replace suture needle 104 by switching switch 284 to the reloading mode.

It is further envisioned that an LED can be utilized to provide feedback to the clinician of the device status such as, e.g., closing/opening of first and second jaws 130, 132, securement of suture needle 104 with first or second jaws 130, 132, etc. Further, the feedback system may further provide the tissue data to the clinician, such as, e.g., thickness of tissue. This can, for example, be achieved by utilizing servomotors, which can be utilized in monitoring the position of first and second jaws 130, 132.

Figure 13:
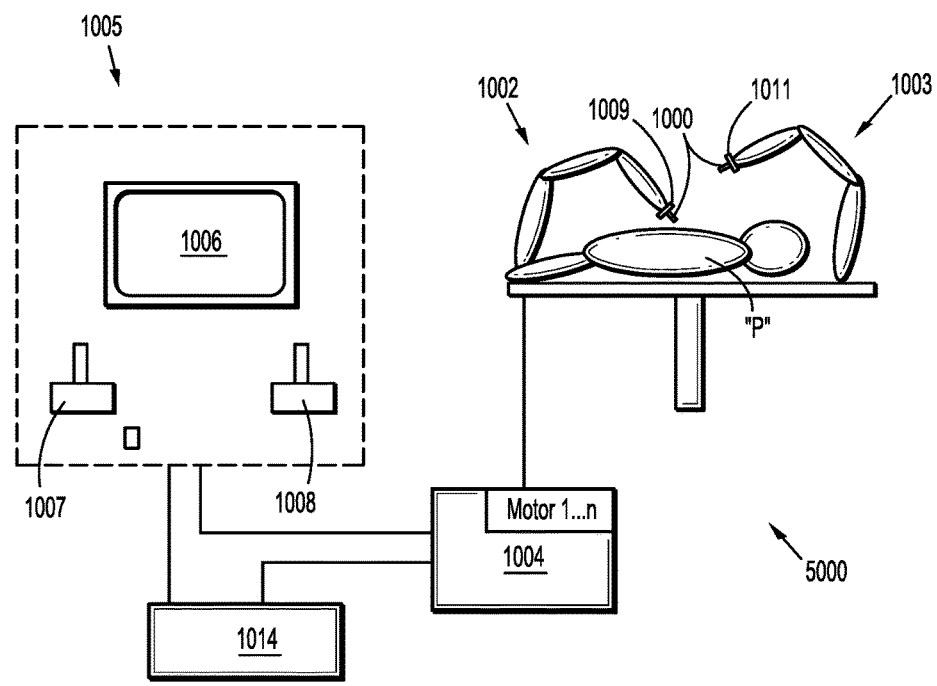
FIG. 13 is a schematic illustration of a robotic surgical system for use with the powered endoscopic suturing device of FIG. 1.

With reference now to FIG. 13, it is also envisioned that powered suturing device 1000 may be adapted for use in a medical work station shown generally as work station 5000. Medical work station 5000 is configured for a minimally invasive surgical procedure performed on a subject "P". Medical work station 5000 generally includes a plurality of robot arms 1002, 1003; a control device 1004; and an operating console 1005 coupled with control device 1004. Operating console 1005 may include a display device 1006 and manual input devices 1007, 1008 to enable the clinician to telemanipulate robot arms 1002, 1003. In addition, medical work station 5000 may also include a database 1014 connected with control device 1004. Database 1014 may include, e.g., pre-operative data from subject "P" and/or anatomical atlases.

Each robot arm 1002, 1003 includes an attaching device 1009, 1011 configured to operatively engage a surgical instrument such as, e.g., powered suturing device 1000. Robot arms 1002, 1003 may be driven by electric drives (not shown) that are connected to control device 1004. Control device 1004, e.g., a computer, may be set up to activate the drives, such that robot arms 1002, 1003 having, e.g., powered suturing device 1000 attached thereto, perform desired functions according to the input of manual input devices 1007, 1008.

Persons skilled in the art will understand that the structures and methods specifically described herein and shown in the accompanying figures are non-limiting exemplary embodiments, and that the description, disclosure, and figures should be construed merely as exemplary of particular embodiments. For example, end effector 100 may be modified to accommodate rotatable or articulatable movement. It is to be understood, therefore, that the present disclosure is not limited to the precise embodiments described, and that various other changes and modifications may be effected by one skilled in the art without departing from the scope or spirit of the disclosure.

Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An endoscopic stitching device, comprising:
   an actuation shaft;
   a tool assembly including a suture needle and a pair of jaws transitionable between open and closed positions, each jaw of the pair of jaws including a needle engaging blade slidably supported thereon, each needle engaging blade transitionable between an extended position in which the needle engaging blade engages the suture needle and a retracted position in which the needle engaging blade is disengaged from the suture needle; and
   a drive assembly including:
      first, second, and third electrical actuators, the second and third electrical actuators operatively coupled with the needle engaging blades to provide axial displacement of the needle engaging blades;
      a first lead screw operatively connected to the first electrical actuator;
      a first nut operatively connected to the actuation shaft, actuation of the first electrical actuator causing rotation of the first lead screw, which, in turn causes the axial displacement of the actuation shaft;
      a second lead screw operatively connected to the second electrical actuator; and
      a second nut operatively connected to one of the needle engaging blades, actuation of the second electrical actuator causing rotation of the second lead screw, which, in turn causes the axial displacement of the one of the needle engaging blades, the axial displacement of the actuation shaft causing opening and closing of the pair of jaws.

2. The endoscopic stitching device according to claim 1, wherein the drive assembly further includes a printed circuit board including a microprocessor to control execution of at least one of the first, second, or third electrical actuators.

3. The endoscopic stitching device according to claim 2, wherein the drive assembly includes a control interface including first and second buttons, actuation of the first button causing reciprocating axial displacement of the needle engaging blades.

4. The endoscopic stitching device according to claim 2, wherein actuation of the second button transitions the pair of jaws between the open and closed positions.

5. The endoscopic stitching device according to claim 2, wherein actuation of the first button transitions the pair of jaws between open and closed positions and causes the reciprocating axial displacement of the needle engaging blades.

6. The endoscopic stitching device according to claim 2, wherein the drive assembly further includes a battery pack to supply power to the first, second, and third electrical actuators.

7. The endoscopic stitching device according to claim 1, wherein each jaw of the pair of jaws defines a needle receiving recess dimensioned to receive a portion of the suture needle.

8. The endoscopic stitching device according to claim 1, wherein at least one of the first, second, or third electrical actuators is a servomotor.

9. The endoscopic stitching device according to claim 1, wherein the drive assembly further includes a third lead screw and a third nut, the third electrical actuator operatively connected to the third lead screw, the third nut operatively connected to the other one of the needle engaging blades, actuation of the third electrical actuator causing rotation of the third lead screw, which, in turn causes the axial displacement of the other one of the needle engaging blades.

10. An endoscopic stitching device, comprising:
a handle assembly including a drive assembly including:
first, second, and third electrical actuators;
a first lead screw operatively connected to the first electrical actuator;
a first nut;
a second lead screw operatively connected to the second electrical actuator; and
a second nut;
an elongate member having an actuation shaft operatively connected to the first nut, actuation of the first electrical actuator causing rotation of the first lead screw, which, in turn causes the axial displacement of the actuation shaft, the elongate member extending from the handle assembly; and
a tool assembly operatively supported on the elongate member, the tool assembly including a suture needle and a pair of jaws pivotally associated with one another, each jaw of the pair of jaws including a needle engaging blade slidably supported thereon, each needle engaging blade transitionable between an extended position in which the needle engaging blade engages the suture needle and a retracted position in which the needle engaging blade is disengaged from the suture needle, the first electrical actuator operatively coupled with the actuation shaft, such that axial displacement of the actuation shaft results in opening and closing of the pair of jaws, the second and third electrical actuators operatively coupled with the respective needle engaging blades to provide axial displacement of the needle engaging blades, the second nut operatively connected to one of the needle engaging blades, actuation of the second electrical actuator causing rotation of the second lead screw, which, in turn causes the axial displacement of the one of the needle engaging blades.

11. The endoscopic stitching device according to claim 10, each jaw of the pair of jaws defines a needle receiving recess dimensioned to receive a portion of the suture needle.

12. The endoscopic stitching device according to claim 10, wherein at least one of the first, second, or third electrical actuators is a servomotor.

13. The endoscopic stitching device according to claim 10, wherein the drive assembly further includes a third lead screw and a third nut, the third electrical actuator operatively connected to the third lead screw, the third nut operatively connected to the other one of the needle engaging blades, actuation of the third electrical actuator causing rotation of the third lead screw, which, in turn causes the axial displacement of the other one of the needle engaging blades.

14. The endoscopic stitching device according to claim 10, wherein the drive assembly further includes a printed circuit board including a microprocessor to control execution and sequence of the at least one of first, second, or third electrical actuators.

15. The endoscopic stitching device according to claim 10, wherein the drive assembly further includes a battery pack to supply power to the first, second, and third electrical actuators.

* * * * *